July 9, 1957 C. W. M. HESS Plant Pat. 1,617
YEW (TAXUS) PLANT
Filed June 5, 1956
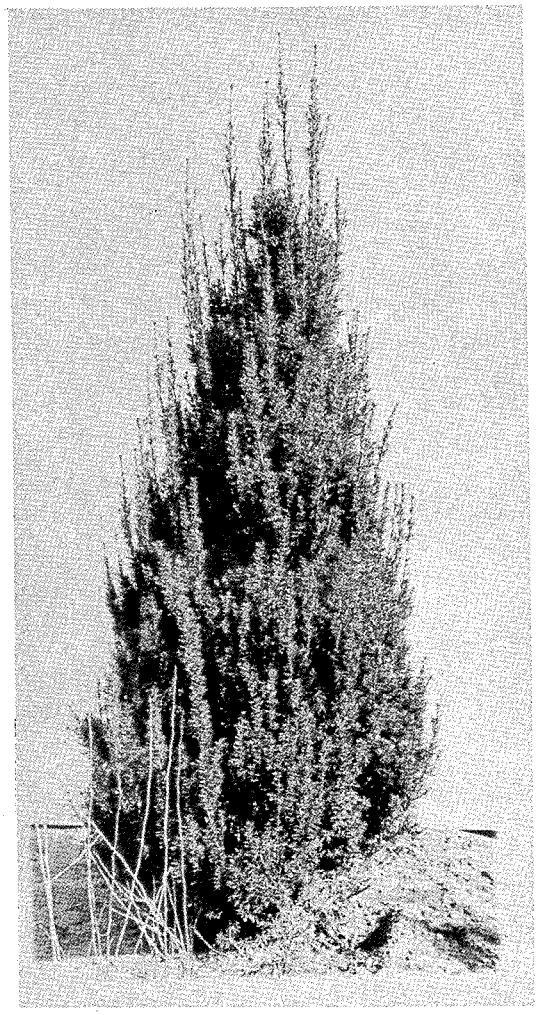
INVENTOR
Cornelius W. M. Hess
By Orville M. Kile
Plant Patent Agent United States Patent Office Plant Pat. 1,617
Patented July 9, 1957

1,617

YEW (TAXUS) PLANT

Cornelius W. M. Hess, Mountain View, N. J.

Application June 5, 1956, Serial No. 589,571

1 Claim. (Cl. 47—59)

My present invention relates to an improvement in decorative yew (Taxus) of the shrub type. It originated as a seedling from a cross made by me at our nurseries in Mountain View, New Jersey, the cross having been between the varieties *Taxus cuspidata capitata* and *Taxus* Moon's *columnaris* (neither patented).

I have asexually reproduced this new variety by means of cuttings, at the New Jersey location, and its distinguishing characteristics appear to be permanent after several years.

The new variety resembles its parent, *Taxus* Moon's *columnaris,* in some respects but differs radically in its growth and form. Like this parent, but unlike most other varieties, it can be propagated readily from any part of the plant and will stand severe cold climate.

The accompanying illustration is a photograph of the original plant of my new variety which now stands 5 feet tall and approximately 29 inches across the base. Its narrow, conical shape is clearly evident in the photograph.

In the following description of my variety, the color plate numbers refer to Ridgway's Color Standards and Nomenclature, whereas any other color nomenclature refers to the usual dictionary meaning.

*The plant*

Type: Evergreen shrub.

Form: Upright; compact; conical. Has single central stem rather than several or many stems. Upright side branches from this central stem give this new variety its characteristic conical shape.

Growth habit: Slow-growing. Retains its compact, conical shape with practically no trimming.

Branches: Upright; slender; strong.

Cold resistance: Withstands cold as low as 15 to 20 degrees below zero F. In the winter of 1942–43 the variety was subjected to these temperatures for a period of five days in our nurseries in New Jersey and was unharmed. Again in the winter of 1947–48 it withstood extended temperatures of 15 degrees below zero F. No tests have been made in climates colder than this. Lower temperatures have not been tested.

Propagation: Can readily be asexually propagated from any part of the plant.

Leaves:

*Shape.*—Linear; needle-like; tapering.

*Color.*—Dark green above, approximately Dark Dull Yellow Green (Plate XXXII) on upper side and Yellowish Olive Green (Pl. XXX) on under side. No claim is made as to novelty of color.

*Arrangement.*—Leaves arranged radially around stem and very close together. Extend upward at an angle of about 45 degrees.

*Size.*—Leaves are less than an inch long, usually ¾ inch, with many at tips of branches only ¼ inch long.

Flowers: Insignificant, appearing on previous year's wood about the first of May.

Fruits:

*Maturity.*—Fruit ripens October to November.

*Quantity.*—Sparse.

*Nutlet.*—Broad ovate with obtuse apex. Dull chestnut brown.

*Aril.*—Light red, covered with white bloom.

*Comparison*

The variety most like my new variety is one of its parents, *Taxus* Moon's *columnaris* (unpatented). The principal differences are as follows:

1. The growth of my new variety is slower and more compact.

2. The form of the plant of my variety is conical rather than the broad cylindrical form of Moon's *columnaris.*

3. My variety grows from a single central stem rather than from the many stems characteristic of Moon's *columnaris.*

4. Fruits of the two varieties differ somewhat. In my variety the fleshy part is lighter in color and smaller in size.

Having thus disclosed my new variety, I claim:

The new and distinct variety of yew (Taxus) plant, substantially as herein shown and described, characterized particularly by its slow, compact growth from a single central stem; the conical form of its plant retained with little or no trimming; its ability to be readily propagated asexually from any portion of the plant; and its tolerance of a climate at least as cold as 15 to 20 degrees below zero F.

No references cited.